(12) United States Patent
Ye et al.

(10) Patent No.: US 12,252,722 B2
(45) Date of Patent: Mar. 18, 2025

(54) METHOD FOR SYNTHESIZING SINGLE-STRANDED DNA

(71) Applicant: Jiangsu Genscript Biotech Co., Ltd., Suzhou (CN)

(72) Inventors: Lumeng Ye, Jiangsu (CN); Haiye Sun, Jiangsu (CN); Yifan Li, Jiangsu (CN); Cheng-Hsien Wu, Jiangsu (CN)

(73) Assignee: Jiangsu Genscript Biotech Co., Ltd., Jiangsu (CN)

( * ) Notice: Subject to any disclaimer, the term of this patent is extended or adjusted under 35 U.S.C. 154(b) by 853 days.

(21) Appl. No.: 17/309,488

(22) PCT Filed: Dec. 27, 2019

(86) PCT No.: PCT/CN2019/128948
§ 371 (c)(1),
(2) Date: Jun. 1, 2021

(87) PCT Pub. No.: WO2020/135651
PCT Pub. Date: Jul. 2, 2020

(65) Prior Publication Data
US 2022/0042059 A1    Feb. 10, 2022

(30) Foreign Application Priority Data
Dec. 28, 2018 (CN) .......................... 201811624165.0

(51) Int. Cl.
*C12P 19/34* (2006.01)
*C12N 15/115* (2010.01)
*C12Q 1/6844* (2018.01)

(52) U.S. Cl.
CPC ............ *C12P 19/34* (2013.01); *C12N 15/115* (2013.01); *C12Q 1/6844* (2013.01); *C12N 2310/16* (2013.01)

(58) Field of Classification Search
None
See application file for complete search history.

(56) References Cited

FOREIGN PATENT DOCUMENTS

| | | |
|---|---|---|
| CN | 102296065 A | 12/2011 |
| CN | 102719550 A | 10/2012 |
| CN | 103255227 A | 8/2013 |
| CN | 105624165 A | 6/2016 |
| CN | 108060191 A | 5/2018 |
| WO | 2007135354 A1 | 11/2007 |
| WO | 2009/120374 A2 | 10/2009 |
| WO | 2018121634 A1 | 7/2018 |

OTHER PUBLICATIONS

International Search Report issued Apr. 2, 2020 in International Application No. PCT/CN2019/128948 (English translation).
Bitinaite, J. et al., "USER Friendly DNA Engineering and Cloning Method by Uracil Excision," Nucleic Acids Research, vol. 35, No. 6 (2007).

*Primary Examiner* — Robert J Yamasaki
(74) *Attorney, Agent, or Firm* — Ice Miller LLP (57) ABSTRACT

A method for synthesizing single-stranded DNA, specifically a process for producing single-stranded DNA without base mutations, is provided, by which single-stranded DNA is produced by uracil-specific excision reagent (USER)-mediated self-looping of double-stranded DNA combined with rolling circle replication.

19 Claims, 4 Drawing Sheets
Specification includes a Sequence Listing.

TCAAACGCTACTACTATTAGTAGAATTGATGCCACCTTTTCAGCTCGCGCCC
CAAATGAAAATATAGCTAAACAGGTTATTGACCATTTGCGAAATGTATCTAA
TGGTCAAACTAAATCTACTCGTTCGCAGAATTGGGAATCAACTGTTACATG
GAATGAAACTTCCAGACACCGTACTTTAGTTGCATATTTAAAACATGTTGAG
CTACAGCACCAGATTCAGCAATTAAGCTCTAAGCCATCCGCAAAAA

FIG. 10

TCAAACGCTACTACTATTAGTAGAATTGATGCCACCTTTTCAGCTCGCGC
CCCAAATGAAAATATAGCTAAACAGGTTATTGACCATTTGCGAAATGTAT
CTAATGGTCAAACTAAATCTACTCGTTCGCAGAATTGGGAATCAACTGTT
ACATGGAATGAAACTTCCAGACACCGTACTTTAGTTGCATATTTAAAACA
TGTTGAGCTACAGCACCAGATTCAGCAATTAAGCTCTAAGCCATCCGCAA
AAATGACCTCTTATCAAAAGGAGCAATTAAAGGTACTCTCTAATCCTGAC
CTGTTGGAGTTTGCTTCCGGTCTGGTTCGCTTTGAAGCTCGAATTAAAAC
GCGATATTTGAAGTCTTTCGGGCTTCCTCTTAATCTTTTTGATGCAATCC
GCTTTGCTTCTGACTATAATAGTCAGGGTAAAGACCTGATTTTTGATTTA
TGGTCATTCTCGTTTTCTGAACTGTTTAAAGCATTTGAGGGGGATTCAAT
GAATATTTATGACGATTCCGCAGTATTGGACGCTATCCAGTCTAAACATT
TTACTATTACCCCCTCTGGCAAAACTTCTTTTGCAAAAGCCTCTCGCTAT
TTTGGTTTTTATCGTCGTCTGGTAAACGAGGGTTATGATAGTGTTGCTCT
TACTATGCCTCGTAATTCCTTTTGGCGTTATGTATCTGCATTAGTTGAAT
GTGGTATTCCTAAATCTCAACTGATGAATCTTTCTACCTGTAATAATGTT
GTTCCGTTAGTTCGTTTTATTAACGTAGATTTTTCTTCCCAACGTCCTGA
CTGGTATAATGAGCCAGTTCTTAAAATCGCATAAGGTAATTCACAATGAT
TAAAGTTGAAATTAAACCATCTCAAGCCCAATTTACTACTCGTTCTGGTG
TTTCTCGTCAGGGCAAGCCTTATTCACTGAATGAGCAGCTTTGTTACGTT
GATTTGGGTAATGAATATCCGGTTCTTGTCAAGATTACTCTTGATGAAGG
TCAGCCAGCCTATGCGCCTGGTCTGTACACCGTTCATCTGTCCTCTTTCA
AAGTTGGTCAGTTCGGTTCCCTTATGATTGACCGTCTGCGCCTCGTTCCG
GCTAAGTAACATGGAGCAGGTCGCGGATTTCGACACAATTATCAGGCGA
TGATACAAATCTCCGTTGTACTTTGTTTCGCGCTTGGTATAATCGCTGGG
GGTCAAAGATGAGTGTTTTAGTGTATTCTTTCGCCTCTTTCGTTTTAGGT
TGGTGCCTTCGTAGTGGCATTACGTATTTTACCCGTTTAATGGAAACTTC
CTCATGAAAAGTCTTTAGTCCTCAAAGCCTCTGTAGCCGTTGCTACCCT

FIG. 11

```
TCAAACGCTACTACTATTAGTAGAAATTGATGCCACCTTTTCAGCTCGCGCCCCAAATGA
AAATATAGCTAAACAGGTTATTGACCATTTGCGAAATGTATCTAATGGTCAAACTAAATC
TACTCGTTCGCAGAATTGGGAATCAACTGTTACATGGAATGAAACTTCCAGACACCGTA
CTTTAGTTGCATATTTAAAACATGTTGAGCTACAGCACCAGATTCAGCAATTAAGCTCTA
AGCCATCCGCAAAAATGACCTCTTATCAAAAGGAGCAATTAAAGGTACTCTCTAATCCT
GACCTGTTGGAGTTTGCTTCCGGTCTGGTTCGCTTTGAAGCTCGAATTAAAACGCGATA
TTTGAAGTCTTTCGGGCTTCCTCTTAATCTTTTTGATGCAATCCGCTTTGCTTCTGACTA
TAATAGTCAGGGTAAAGACCTGATTTTTGATTTATGGTCATTCTCGTTTTCTGAACTGTT
TAAAGCATTTGAGGGGGATTCAATGAATATTTATGACGATTCCGCAGTATTGGACGCTAT
CCAGTCTAAACATTTTACTATTACCCCCTCTGGCAAAACTTCTTTTGCAAAAGCCTCTC
GCTATTTGGTTTTTATCGTCGTCTGGTAAACGAGGGTTATGATAGTGTTGCTCTTACTAT
GCCTCGTAATTCCTTTGGCGTTATGTATCTGCATTAGTTGAATGTGGTATTCCTAAATCT
CAACTGATGAATCTTCTACCTGTAATAATGTTGTTCCGTTAGTTCGTTTTATTAACGTAG
ATTTTTCTTCCCAACGTCCTGACTGGTATAATGAGCCAGTTCTTAAAATCGCATAAGGTA
ATTCACAATGATTAAAGTTGAAATTAAACCATCTCAAGCCCAATTTACTACTCGTTCTGG
TGTTTCTCGTCAGGGCAAGCCTTATTCACTGAATGAGCAGCTTTGTTACGTTGATTTGG
GTAATGAATATCCGGTTCTTGTCAAGATTACTCTTGATGAAGGTCAGCCAGCCTATGCG
CCTGGTCTGTACACCGTTCATCTGTCCTCTTTCAAAGTTGGTCAGTTCGGTTCCCTTATG
ATTGACCGTCTGCGCCTCGTTCCGGCTAAGTAACATGGAGCAGGTCGCGGATTTCGAC
ACAATTTATCAGGCGATGATACAAATCTCCGTTGTACTTTGTTTCGCGCTTGGTATAATC
GCTGGGGGTCAAAGATGAGTGTTTTAGTGTATTCTTTCGCCTCTTTCGTTTTAGGTGGT
GCCTTCGTAGTGGCATTACGTATTTTACCCGTTTAATGGAAACTTCCTCATGAAAAAGTC
TTTAGTCCTCAAAGCCTCTGTAGCCGTTGCTACCCTCGTTCCGATGCTGTCTTTCGCTGC
TGAGGGTGACGATCCCGCAAAAGCGGCCTTTAACTCCTGCAAGCCTCAGCGACCG
AATATATCGGTTATGCGTGGGCGATGGTTGTTGTCATTGTCGGCGCAACTATCGGTATCA
AGCTGTTTAAGAAATTCACCTCGAAAGCAAGCTGATAAACCGATACAATTAAAGGCTC
CTTTTGGAGCCTTTTTTTTTGGAGATTTTCAACGTGAAAAAATTATTATTCGCAATTCCT
TTAGTTGTTCCTTTCTATTCTCACTCCGCTGAAACTGTTGAAAGTTGTTTAGCAAAACC
CCATACAGAAAATTCATTTACTAACGTCTGGAAAGACGACAAAACTTTAGATCGTTACG
CTAACTATGAGGGTTGTCTGTGGAATGCTACAGGCGTTGTAGTTTGTACTGGTGACGAA
ACTCAGTGTTACGGTACATGGGTTCCTATTGGGCTTGCTATCCCTGAAAATGAGGGTGG
TGGCTCTGAGGGTGGCGGTTCTGAGGGTGGCGGTTCTGAGGGTGGCGGTACTAAACCT
CCTGAGTACGGTGATACACCTATTCCGGGCTATACTTATATCAACCCTCTCGACGGCACT
TATCCGCCTGGTACTGAGCAAAACCCCGCTAATCCTAATCCTTCTCTTGAGGAGTCTCA
GCCTCTTAATACTTTCATGTTTCAGAATAATAGGTTCCGAAATAGGCAGGGGCATTAA
CTGTTTATACGGGCACTGTTACTCAAGGCACTGACCCCGTTAAAACTTATTACCAGTAC
ACTCCTGTATCATCAAAAGCCATGTATGACGCTTACTGGAACGGTAAATTCAGAGACTG
CGCTTTCCATTCTGGCTTTAATGAGGATCCATTCGTTTGTGAATATCAAGGCCAATCGTC
TGACCTGCCTCAACCTCCTGTCAATGCTGGCGGCGGCTCTGGTGGTGGTTCTGGTGGC
GGCTCTGAGGGTGGTGGCTCTGAGGGTGGCGGTT
```

FIG. 12

METHOD FOR SYNTHESIZING SINGLE-STRANDED DNA

CROSS-REFERENCE TO RELATED APPLICATIONS

This application is a Section 371 of International Application No. PCT/CN2019/128948, filed on Dec. 27, 2019, which published in the Chinese language on Jul. 2, 2020 under International Publication No. WO 2020/135651 A1, which claims priority to Chinese Application No. 201811624165.0, filed on Dec. 28, 2018. Each disclosure is incorporated herein by reference in its entirety.

REFERENCE TO SEQUENCE LISTING SUBMITTED ELECTRONICALLY

This application contains a sequence listing, which is submitted electronically as an ASCII formatted sequence listing with a file name "065824_9US1 Sequence Listing" and a creation date of Jan. 10, 2025, and having a size of 6,959 bytes. The sequence listing submitted electronically is part of the specification and is herein incorporated by reference in its entirety.

BACKGROUND

Technical Field

The present invention relates to the field of bioengineering, and in particular to a process for producing single-stranded DNA without base mutation.

Related Art

In gene repair and functional foreign gene insertion, single-stranded DNA templates have shown many advantages over double-stranded DNA templates in various aspects, for example, higher editing efficiency and less cytotoxicity to fragile mammalian cells, as well as lower editing error/off-target rate, a factor crucial for gene therapy. However, at present, due to the difficult technique, high cost, and low yield, single-stranded DNA templates are extremely expensive, which greatly limits the cost of this method in research. The chemically synthesized single-stranded DNA templates have a length limit of 200 bases, and the wrong sequence contained in the product cannot be removed by the conventional downstream purification method. Commonly used methods for producing single-stranded DNA samples include exonuclease digestion, asymmetric PCR, and magnetic bead adsorption. However, all of the above methods have disadvantages. For example, the exonuclease will non-specifically degrade the target band while digesting the antisense strand, so that it is impossible to provide a product that exactly meets the requirements. Asymmetric PCR is a low-cost production method, but the requirement for production efficiency in terms of the sequence is uncertain, making the production effect uncontrollable and the method is not suitable for stable production. Although the biotin-streptavidin magnetic bead adsorption is simple in operation and stable in production, the imported high-quality magnetic beads are expensive and require long period of waiting time after purchase, making it a high hazard to allow the core production technology to rely on an imported product.

SUMMARY

To develop a single-stranded DNA template sample with higher purity, higher production and lower price, the inventors develop a universal and high-efficiency process for producing long single-stranded DNA by uracil-specific excision reagent (USER)-mediated self-looping of double-stranded DNA combined with auto-folding during the annealing process of single-stranded DNA achieved by a special sequence design, a type II restriction endonuclease that can accurately cleave a target single-stranded fragment, and rolling circle replication of thermostatically amplified single-stranded DNA.

An object of the present invention is to develop a process for producing single-stranded DNA with high dose, high purity, and high sequence fidelity, to solve the problem of high price and low yield of such products. This process can increase the yield of single-stranded DNA of 200 nt or longer from a few ug to hundreds of ug, to reach the nmol level; and also increase the yield of single-stranded DNA with a length of 1350 nt from a few ug to tens of ug.

As an example, the process of the present invention may include the following steps:

Step 1 (sequence analysis process): Bioinformatics analysis of a target DNA sequence (for example, any DNA sequence with a length of 150-2500 nt) is performed, to check the type II restriction endonuclease recognition and cleavage site contained in the sequence. A commonly used type II restriction endonuclease having a recognition sequence that is not included in the target sequence, such as BsaI, is selected, and the sequence of a cleavage site thereof is determined for the design of aptamer sequences and universal primers on both sides of the target sequence.

Step 2 (primer design process): A left aptamer sequence and a right aptamer sequence are respectively added to two ends of the target sequence, and undergo gene synthesis together. The left aptamer sequence includes, from the 5' to 3' terminus, a homology arm (at least 4 nucleotides, preferably 6-10 nucleotides, such as 8 nucleotides), one T nucleotide, the selected type II restriction endonuclease recognition site, and optionally an additional sequence of 1 or several nucleotides in sequence. The additional sequence and the selected type II restriction endonuclease recognition site constitute the type II restriction endonuclease cleavage site (where in some embodiments, the type II restriction endonuclease recognition site is the same as the cleavage site, and the additional sequence is absence in this case), so that the type II restriction endonuclease can cleave at the 3' terminus of the additional residue sequence. The right aptamer sequence includes, from the 5' to 3' terminus, a reverse complementary sequence of the selected type II restriction endonuclease recognition site and a homology arm. The homology arm is the same as the homology arm in the left aptamer sequence, but is 1-3 nucleotides less at the 3' terminus. At the 5' terminus of the reverse complementary sequence of the recognition site, an optional additional sequence of one or several nucleotides is present. The additional sequence and the reverse complementary sequence of the recognition site constitute the type II restriction endonuclease cleavage site (where in some embodiments, the type II restriction endonuclease recognition site is the same as the cleavage site, and the additional sequence is absence in this case) Preferably; the length of the left and right aptamer sequences differs by 1-4 bases.

Step 3 (template amplification and production: self-looping): The fragment for gene synthesis containing left and right aptamer sequences at two ends is amplified by PCR using a forward and a reverse primer containing uracil (U) modification, where the U modification is located at 3' terminus of the sequence corresponding to the homology arm in the primer sequence. The product is purified, and the purified product is digested with USER (New England BioLabs Inc.) to cleave at the uracil to produce cohesive terminuses, and the two cohesive terminuses are than ligated by T4 DNA ligase (New England BioLabs Inc.), such that the amplified product is self-looped to produce a gapped dsDNA circle, which can be used as a substrate for rolling circle replication.

The template amplification is a conventional PCR operation process, in which the reaction system depends on the specific DNA polymerase and buffer used, the annealing temperature of the PCR reaction depends on the specific primer sequence, and the extension time of the PCR reaction depends on the specific length of the template sequence.

The self-looping reaction system for producing gapped circular double-stranded DNA using USER and T4 DNA ligase comprises 100 ng purified double-stranded DNA template product, 1 ul 10×T4 DNA ligase reaction buffer, 1 ul USER, 1 ul T4 DNA ligase, and ddH$_2$O added up to a final total reaction system of 10 ul. The reaction comprises incubation at 37° C. for 30 min and then at 20° C. for 30 min, followed by cooling to and storage at 4° C.

Step 4 (rolling circle replication): In a 200 ul PCR tube, 100 ng of the gapped circular DNA sample produced in Step 3 is added to 10 ul of 10× amplification buffer (500 mM Tris-HCl, 50 mM MgCl$_2$, 750 mM KCl, 40 mM DTT, pH 8.2, 25° C.), 10.0 ul BSA(2 mg/ml), 1.0 ul dNTP (10 mM), 5 ul phi29 DNA polymerase (5 U/ul), and ddH$_2$O added up to a final total reaction system of 100 ul, amplified at 30° C. for 4-8 hrs, treated at 65° C. for 10 min, and then cooled to 4° C.

Step 5 (annealing—auto-folding): The PCR tube after rolling circle replication is subjected to the following annealing procedure to form a hairpin structure: 5 min at 80° C., cooling to 65° C. at 0.1° C./s, 5 min at 65° C., cooling to 42° C. at 0.1° C./s, 5 min at 42° C., 5 min at 37° C., cooling to 4° C. at 0.1° C./s, and then stored at 4° C.

Step 6 (restriction endonuclease cleavage-release of the target fragment, that is, the long single-stranded monomer): 15 ul of 10× restriction endonuclease buffer, and 2 ul of the selected type II restriction endonuclease are added to the above reaction product, and ddH$_2$O is added up to a volume of 150 ul. The system is stood at an optimal reaction temperature for the restriction endonuclease for 60 min, and then thermally denatured and inactivated.

Step 7 (purification and concentration): The restriction endonuclease cleavage product contains the single-stranded DNA product of the target fragment, the hairpin structure, and other unknown DNA fragments when the target fragment is greater than 300 nt. The product can be recovered by magnetic bead adsorption or by extraction by agarose gel electrophoresis according to the actual scenario during production and use, and then concentrated by lyophilization or precipitation in isopropanol.

Specifically, this application provides the following technical solutions:

1. A method for producing a target single-stranded DNA, comprising:

(1) obtaining a template double-stranded DNA molecule consisting of a first strand and a reverse complementary second strand, where the sequence structure of the first strand is as shown in Formula (I):

5' left aptamer sequence-target single-stranded DNA sequence-right aptamer sequence 3'    (I)

where:

the left aptamer sequence has a sequence structure of Formula: $X_n TX_q X_A$; and the right aptamer sequence has a sequence structure of Formula: $X_B X_q' X_{n-m}$ in which $X_n$ is a nucleotide sequence consisting of n nucleotides, where the 5'-terminal nucleotide is A and n is any integer of at least 4;

$X_q$ is the sequence of a type II restriction endonuclease recognition site, and $X_q$ is not present in the target single-stranded DNA sequence; $X_q'$ is a reverse complementary sequence of $X_q$; $X_A$ and $X_B$ are optionally of 0 to several nucleotides, so that $X_q X_A$ and $X_B X_q'$ constitute the cleavage site of the type II restriction endonuclease respectively, to allow the type II restriction endonuclease to cleave at the 3' terminus of the $X_q X_A$ sequence and the 5' terminus of the $X_B X_q'$ sequence;

$X_{n-m}$ is a sequence of n-m nucleotides from the 5' terminus of $X_n$, and m is an integer of 1-3; and A represents the adenine nucleotide; and T represents the thymine nucleotide;

(2) with the template double-stranded DNA molecule as a template, performing PCR amplification using a forward primer and a reverse primer to obtain a product double-stranded DNA molecule comprising a first strand containing the target single-stranded DNA sequence and a reverse complementary second strand thereof;

where the forward primer comprises a sequence of $X_n U X_q X_A$, and the reverse primer comprises a sequence of $X_{n-m}' X_q X_B'$, in which $X_n$, $X_q$, $X_A$, and $X_B$ are the same as in (1); $X_{n-m}'$ is a reverse complementary sequence of $X_{n-m}$, with the T at the 3' terminus being replaced by U; $X_B'$ is a reverse complementary sequence of $X_B$; and U is the uracil nucleotide;

(3) cleaving the product double-stranded DNA molecule at U contained in the two strands with a uracil-specific excision reagent (USER) to produce cohesive terminuses at the two ends of the product double-stranded DNA molecule;

(4) ligating the two cohesive terminuses of the product double-stranded DNA molecule in the presence of a ligase, to form a circular double-stranded DNA having a gap in the first strand;

(5) subjecting the circular double-stranded DNA obtained in Step (4) to rolling circle replication, where the replication starts with the gap in the first strand of the product double-stranded DNA molecule and uses the second strand as the template, to obtain a replicon comprising multiple sequence structures as shown in the following formula (II) in tandem:

-$X_n TX_q X_A$-target single-stranded DNA sequence-$X_B X_q'$-    (II)

(6) annealing the replicon, so that a hairpin structure is formed between two adjacent target single-stranded DNA sequences in the replicon, where preferably the hairpin structure consists of a sequence of $X_q' X_n TX_q$;

(7) treating the replicon with the type II restriction endonuclease, and cleaving at the 5' terminus and 3 terminus of the $X_B X_q'$ $X_n TX_q X_A$ sequence between adjacent target single-stranded DNA sequences to release multiple target single-stranded DNA sequences.

2. The method according to Item 1, where the type II restriction endonuclease is selected from AlwI, BbsI, BbvI, BceAI, BCIVI, BfuAI, BmrI, BpmI, BpuEI, BsaI, BseRI, BsgI, BsmAI, BsmBI, BsmFI, BspMI, BspQI, HphI, HpyAV, FokI, FauI, and HgaI.

3. The method according to any one of Items 1 and 2, where the uracil-specific excision reagent is a uracil-specific excision enzyme (USER™).

4. The method according to any one of Items 1 to 3, where the ligase is T4 DNA ligase.

5. The method according to any one of Items 1 to 4, where Steps (3) and (4) occur in the same reaction system in the presence of the uracil-specific excision reagent and the ligase.

6. The method according to any one of Items 1 to 5, where the rolling circle replication is carried out using a DNA polymerase capable of continuous replication, preferably phi29 DNA polymerase.

7. The method according to any one of Items 1 to 6, where the type II restriction endonuclease is BspQI.

8. The method according to Item 7, where $X_q X_A$ has a sequence of GCTCTTCN, in which N is A, T, C or G, and preferably A; $X_B X_q'$ has a sequence of $N_1 N_2 N_3 N_4$GAAGAGC, in which $N_1$, $N_2$, $N_3$, and $N_4$ are independently selected from A, T, C or G; and more preferably, $X_B X_q'$ has a sequence of CCTT GAAGAGC (SEQ ID NO:8).

9. The method according to any one of Items 1 to 8, where n is 6-10.

10. The method according to any one of Items 1 to 9, where n is 8.

11. The method according to any one of Items 1 to 10, where m is 1.

12. The method according to any one of Items 1 to 11, where $X_n$ has a sequence of AACTATAC, and $X_{n-m}$ has a sequence of AACTATA.

13. The method according to any one of Items 1 to 12, where the target single-stranded DNA has a length of 150-2500 nt.

14. The method according to any one of Items 1 to 13, comprising: performing sequence analysis of the target single-stranded DNA sequence before the template double-stranded DNA molecule is produced, and selecting a type II restriction endonuclease that has no cleavage site in the target single-stranded DNA sequence.

15. A kit for amplifying a target DNA sequence, comprising:
a left aptamer, having a sequence as shown in a formula of $X_n T X_q X_A$; and a right aptamer, having a sequence as shown in a formula of $X_B X_q' X_{n-m}$,
in which $X_n$ is a nucleotide sequence consisting of n nucleotides, where the 5'-terminal nucleotide is A and n is any integer of at least 4, preferably 6-8, and more preferably 8;
$X_q$ is the sequence of a type II restriction endonuclease recognition site, and $X_q$ is not present in the target single-stranded DNA sequence; $X_q'$ is a reverse complementary sequence of $X_q$; $X_A$ and $X_B$ are optionally of 0 to several nucleotides, so that $X_q X_A$ and $X_B X_q'$ constitute the cleavage site of the type II restriction endonuclease respectively, to allow the type II restriction endonuclease to cleave at the 3' terminus of $X_A$ and the 5' terminus of the $X_B$;
$X_{n-m}$ is a sub-sequence of n-m nucleotides from the 5' terminus of $X_n$, and m is an integer of 1-3; and
A represents the adenine nucleotide; and T represents the thymine nucleotide.

15. The kit according to Item 14, further comprising:
a forward primer having a sequence of $X_n U X_q X_A$, and a reverse primer having a sequence of $X_{n-m}' X_q' X_B'$,
where $X_n$, $X_q$, $X_A$, and $X_B$ are the same as in the aptamer; and $X_{n-m}'$ is a reverse complementary sequence of $X_{n-m}$, with T at the 3' terminus being replaced by U; $X_B'$ is a reverse complementary sequence of $X_B$; and U is the uracil nucleotide; and
where the forward primer and the reverse primer allow PCR amplification using the target DNA sequence as a template.

16. A kit for producing single-stranded DNA, comprising:
a DNA polymerase suitable for polymerase chain reaction;
a DNA ligase, preferably T4 DNA ligase;
a uracil specific excision reagent, preferably uracil specific excision enzyme;
a DNA polymerase suitable for rolling circle amplification, preferably phi29 DNA polymerase; and
a type II restriction endonuclease.

17. The kit according to Item 16, further comprising a left aptamer and a right aptamer as defined in Item 14, and a forward primer and a reverse primer as defined in Item 15.

18. The kit according to Item 16 or 17, where the DNA ligase and the uracil-specific excision reagent are placed in the same container.

Beneficial Effects

The process for preparing single-stranded DNA developed in the present invention forms a high-quality single-stranded DNA template method. Since most of the operation steps are carried out by constant-temperature incubation, the process has high adaptability to the production equipment and large-scale production. The raw materials are conventional primers and enzyme preparations, and there is no need for expensive imported streptavidin modified magnetic beads. When a large amount (tens of ug) of single-stranded DNA is prepared, the cost is much lower.

BRIEF DESCRIPTION OF THE DRAWINGS

FIG. 10 shows the sequence of the product prepared in Example 1 determined by next generation sequencing (NGS).

FIG. 11 shows the sequence of the product prepared in Example 2 determined by next generation sequencing (NGS).

FIG. 12 shows the sequence of the product prepared in Example 3 determined by next generation sequencing (NGS).

DETAILED DESCRIPTION

For further understanding of the method of the present invention, the present invention will be further described in conjunction with examples.

Example 1

In this example, 48 µg of single-stranded DNA with a length of 253 nt was prepared by the present process, with a purity of 91% and a sequence accuracy of 100%:

The test sample was a DNA sequence with a length of 253 nt (SEQ ID NO: 1).

The production process of the single-stranded DNA in this example was as follows.

1) Step 1 (sequence analysis process): After analysis by bioinformatics software, the sequence was found to have no BspQI restriction cleavage site, so BspQI was selected as the final cleavage enzyme.
2) Step 2 (primer design process): 5'-AAC-TATACTGCTCTTCA-3' (SEQ ID NO:4) and 5'-CCTTGAAGAGCAACTATA-3' (SEQ ID NO: 5) were respectively added to two ends of the target sequence, and subjected to gene synthesis. The primers for PCR were the forward primer Pf: 5'-AAC-TATACUGCTCTTCA-3' (SEQ ID NO:6) and the reverse primer Pr: 5'-TATAGTUGCTCTTCAAGG-3' (SEQ ID NO:7). The primers were synthesized.
3) Step 3 (template amplification and production-self-looping): Using primers (Pf, Pr) with uracil modification, the synthesized fragment with terminal aptamers were amplified. The PCR reaction system was:

| Reaction system (100 uL): | |
|---|---|
| Reagent<br>253 (288 bp) | Volume<br>uL |
| 5*phusion HF buffer | 20 |
| 10 mM dNTPs | 2 |
| 100% DMSO | 3 |
| 253 UF (50 uM) | 1 |
| 253 UR (50 uM) | 1 |
| DNA template | 1 |
| phusion U Hot Start DNA polymerase | 1 |
| ddH2O | 71 |

PCR Reaction Procedure

| Reaction condition | |
|---|---|
| 98° C. | 30 s |
| 98° C. | 10 s |
| 63° C. | 30 s |
| 72° C. | 8 s |
| 72° C. | 5 min |
| 4° C. | Long time |

30 Cycles

Figure 1:
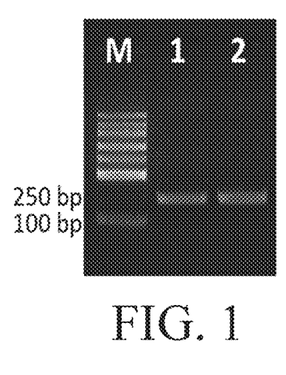
FIG. 1 shows the result of agarose gel electrophoresis of the product obtained by PCR amplification of the synthesized fragment with terminal aptamers using primers modified with uracil in Example 1.

The electropherogram of the PCR product is shown in FIG. 1.

Then the PCR product was recovered, and self-looped. The reaction system for producing gapped circular double-stranded DNA by self-looping using USER enzyme and T4 DNA ligase is:

| | Total amount of<br>PCR product:<br>100 ng<br>uL |
|---|---|
| 253-U | 0.48 |
| 10*T4 ligase buffer | 1 |
| USER | 1 |
| T4 ligase | 0.50 |
| ddH2O | 7.02 |

The reaction conditions include 30 min at 37° C., 30 min at 20° C., and storage at 4° C.

4) Step 4 (rolling circle replication): In a 200 ul PCR tube, 100 ng of the gapped circular DNA sample produced in Step 3 was subjected to rolling circle replication by incubation at 30° C. for 4-8 hrs, and then inactivated at 80° C. for 20 min. The reaction system for rolling circle replication is:

(For example, in 100 ul)

| Reagent | uL |
|---|---|
| USER treatment sample | 10 |
| 10*phi29 DNA polymerase buffer | 10 |
| dNTP(10 mM) | 5 |
| BSA(2 mg/mL) | 10 |
| phi29 DNA polymerase | 5 |
| ddH2O | 60 |

Figure 2:
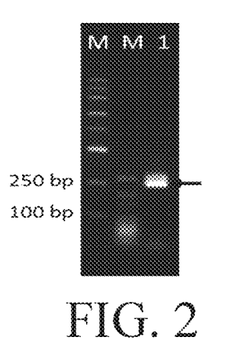
FIG. 2 shows the result of agarose gel electrophoresis of the target fragment that is a long single-stranded monomer released after the hairpin structure is cleaved by BspQI restriction endonuclease in Example 1.
Figure 3:
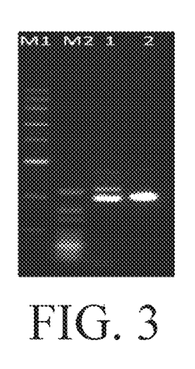
FIG. 3 shows the result of agarose gel electrophoresis before and after magnetic bead purification of the product obtained after the hairpin structure is cleaved by BspQI restriction endonuclease in Example 1, where Lane 1 is the crude product before purification, and Lane 2 is the product after magnetic bead purification.
Figure 4:
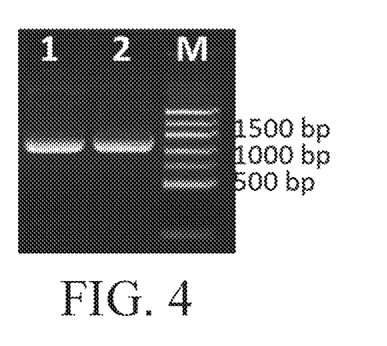
FIG. 4 shows the result of agarose gel electrophoresis of the product obtained by PCR amplification of the synthesized fragment with terminal aptamers using primers modified with uracil in Example 2.

5) Step 5 (annealing—auto-folding): The product after rolling circle replication was annealed by cooling to form a designed hairpin structure, where the annealing procedure was 5 min at 80° C., cooling to 65° C. at 0.1° C./s, 5 min at 65° C., cooling to 42° C. at 0.1° C./s, 5 min at 42° C., 5 min at 37° C., cooling to 4° C. at 0.1° C./s, and then stored at 4° C.
6) Step 6 (restriction endonuclease cleavage-release of the target fragment, that is, the long single-stranded monomer): 15 ul of 10× restriction endonuclease buffer, and 2 ul of the selected type II restriction endonuclease were added to the above reaction product, and ddH$_2$O was added up to a volume of 150 ul. The system was stood at an optimal reaction temperature for the restriction endonuclease for 60 min, and then thermally denatured and inactivated. The electropherogram of the crude reaction product is shown in FIG. 2.
7) Step 7 (purification and concentration): The cleavage product by restriction endonuclease contains the single-stranded DNA product of the target fragment and the hairpin structure. Since the length of the target sequence is less than 300 nt, magnetic beads are used for efficient purification. The comparison before and after purification is shown in FIG. 3. Lane 1 is the crude product before purification, and Lane 2 is the product after magnetic bead purification. The hairpin structure is effectively removed, and the purity is 91%. Next generation sequencing (NGS) was used for sequence verification. The test result of the sequence is shown in FIG. 10, and is consistent with SEQ ID NO: 1.

Example 2

In this example, 40 μg of long single-stranded DNA (SEQ ID NO: 2) with a length of 1350 nt was prepared by the present process with a purity of 97% and a sequence accuracy of 100%.

The test sample was a DNA sequence with a length of 1350 nt.

The production process of the long single-stranded DNA in this example was as follows.

1) Step 1 (sequence analysis process): After analysis by bioinformatics software, the sequence was found to have no BspQI restriction cleavage site, so BspQI was selected as the final cleavage enzyme.
2) Step 2 (primer design process): 5'-AAC-TATACTGCTCTTCA-3' (SEQ ID NO:4) and 5'-CCTTGAAGAGCAACTATA-3' (SEQ ID NO:5) were respectively added to two ends of the target sequence, and subjected to gene synthesis. The primers for PCR were the forward primer Pf: 5'-AAC-TATACUGCTCTTCA-3' (SEQ ID NO:6) and the reverse primer Pr: 5'-TATAGTUGCTCTTCAAGG-3' (SEQ ID NO:7). The primers were synthesized.
3) Step 3 (template amplification and production-self-looping): Using primers (Pf, Pr) with uracil modification, the synthesized fragment with terminal aptamers were amplified. The PCR reaction system was:

| Reaction system (100 uL): | |
|---|---|
| Reagent 1350 | Volume uL |
| 5*phusion HF buffer | 20 |
| 10 mM dNTPs | 2 |
| 100% DMSO | 3 |
| 1350 UF (50 uM) | 1 |
| 1350 UR (50 uM) | 1 |
| DNA template | 1 |
| phusion U Hot Start DNA polymerase | 1 |
| ddH2O | 71 |

PCR Reaction Procedure

| Reaction condition | |
|---|---|
| 98° C. | 30 s |
| 98° C. | 10 s |
| 63° C. | 30 s |
| 72° C. | 1 min |
| 72° C. | 5 min |
| 4° C. | Long time |

30 Cycles

Figure 5:
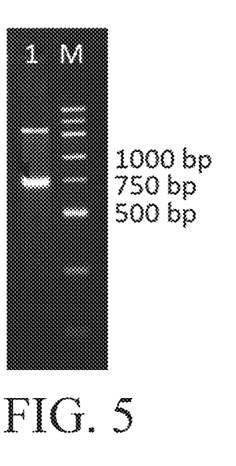
FIG. 5 shows the result of agarose gel electrophoresis of the target fragment that is a long single-stranded monomer released after the hairpin structure is cleaved by BspQI restriction endonuclease in Example 2.

The electropherogram of the PCR product is as shown in FIG. 5.

Then the PCR product was recovered, and self-looped. The reaction system for producing gapped circular double-stranded DNA by self-looping using USER enzyme and T4 DNA ligase is:

| | Total amount of PCR product: 100 ng uL |
|---|---|
| 253-U | 0.48 |
| 10*T4 ligase buffer | 1 |
| USER | 1 |
| T4 ligase | 0.50 |
| ddH2O | 7.02 |

The reaction conditions include 30 min at 37° C., 30 min at 20° C., and storage at 4° C.

4) Step 4 (rolling circle replication): In a 1.5 ml centrifuge tube, 100 ng of the gapped circular DNA sample produced in Step 3 was subjected to rolling circle replication by incubation at 30° C. for 4-8 hrs, and then inactivated at 80° C. for 20 min. The reaction system for rolling circle replication is (8 ml reaction system):

| Reagent | uL |
|---|---|
| USER treatment sample | 800 |
| 10*phi29 DNA polymerase buffer | 800 |
| dNTP(10 mM) | 400 |
| BSA(2 mg/mL) | 800 |
| phi29 DNA polymerase | 200 |
| ddH2O | 4800 |

Figure 6:
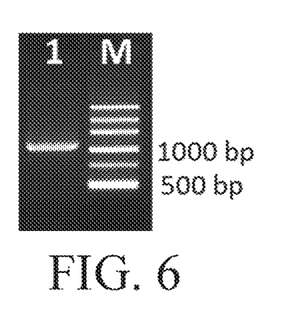
FIG. 6 shows the result of agarose gel electrophoresis after magnetic bead purification of the product obtained after the hairpin structure is cleaved by BspQI restriction endonuclease in Example 2.

5) Step 5 (annealing—auto-folding): The product after rolling circle replication was annealed by cooling to form a designed hairpin structure, where the annealing procedure was 5 min at 80° C., cooling to 65° C. at 0.1° C./s, 5 min at 65° C., cooling to 42° C. at 0.1° C./s, 5 min at 42° C., 5 min at 37° C., cooling to 4° C. at 0.1° C./s, and then stored at 4° C.
6) Step 6 (restriction endonuclease cleavage-release of the target fragment, that is, the long single-stranded monomer): 150 ul of 10× restriction endonuclease buffer, and 20 ul of the selected type II restriction endonuclease were added to the above reaction product, and ddH₂O was added up to a volume of 1500 ul. The system was stood at an optimal reaction temperature for the restriction endonuclease for 60 min, and then thermally denatured and inactivated. The electropherogram of the crude reaction product is shown in FIG. 5.
7) Step 7 (purification and concentration): The cleavage product by restriction endonuclease contains the single-stranded DNA product of the target fragment and the hairpin structure. Since the length of the target sequence is >300 nt, agarose gel electrophoresis is used for extraction and purification. The electropherogram of the purified product is shown in FIG. 6, where Lane 1 is the purified product. The hairpin structure and the double-stranded DNA contaminant are effectively removed, the purity is 97%, and the sequence accuracy is 100%. Next generation sequencing (NGS) was used for sequence verification. The test result of the sequence is shown in FIG. 11, and is consistent with SEQ ID NO: 2.

Example 3

In this example, 10 μg of long single-stranded DNA (SEQ ID NO: 3) with a length of 2350 nt was prepared by the present process with a purity of 93% and a sequence accuracy of 100%.

The test sample was a DNA sequence with a length of 2350 nt.

The production process of the long single-stranded DNA in this example was as follows.

1) Step 1 (sequence analysis process): After analysis by bioinformatics software, the sequence was found to have no BspQI restriction cleavage site, so BspQI was selected as the final cleavage enzyme.
2) Step 2 (primer design process): 5'-AAC-TATACTGCTCTTCA-3' (SEQ ID NO:4) and 5'-CCTTGAAGAGCAACTATA-3' (SEQ ID NO:5) were respectively added to two ends of the target sequence, and subjected to gene synthesis. The primers for PCR were the forward primer Pf: 5'-AAC-TATACUGCTCTTCA-3' (SEQ ID NO:6) and the reverse primer Pr: 5'-TATAGTUGCTCTTCAAGG-3' (SEQ ID NO:7). The primers were synthesized.
3) Step 3 (template amplification and production-self-looping): Using primers (Pf, Pr) with uracil modification, the synthesized fragment with terminal aptamers were amplified. The PCR reaction system was:

| Reaction system (100 uL): | |
|---|---|
| Reagent 1350 | Volume uL |
| 5*phusion HF buffer | 20 |
| 10 mM dNTPs | 2 |
| 100% DMSO | 3 |
| 1350 UF (50 uM) | 1 |
| 1350 UR (50 uM) | 1 |
| DNA template | 1 |
| phusion U Hot Start DNA polymerase | 1 |
| ddH2O | 71 |

PCR Reaction Procedure

| Reaction condition | |
|---|---|
| 98° C. | 30 s |
| 98° C. | 10 s |
| 63° C. | 30 s |
| 72° C. | 2 min |
| 72° C. | 5 min |
| 4° C. | Long time |

30 Cycles

Figure 7:
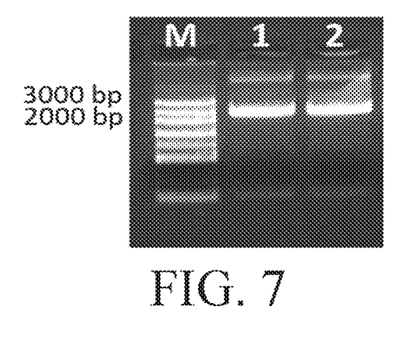
FIG. 7 shows the result of agarose gel electrophoresis of the product obtained by PCR amplification of the synthesized fragment with terminal aptamers using primers modified with uracil in Example 3.
Figure 8:
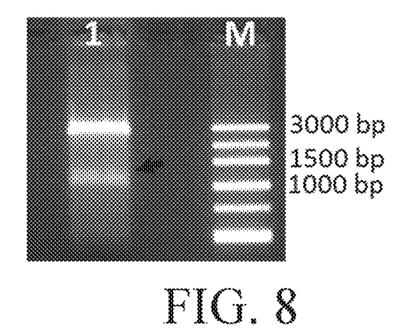
FIG. 8 shows the result of agarose gel electrophoresis of the target fragment that is a long single-stranded monomer released after the hairpin structure is cleaved by BspQI restriction endonuclease in Example 3.

The electropherogram of the PCR product is shown in FIG. 7.

Then the PCR product was recovered, and self-looped. The reaction system for producing gapped circular double-stranded DNA by self-looping using USER enzyme and T4 DNA ligase is:

| | Total amount of PCR product: 100 ng uL |
|---|---|
| 253-U | 0.48 |
| 10*T4 ligase buffer | 1 |
| USER | 1 |
| T4 ligase | 0.50 |
| ddH2O | 7.02 |

The reaction conditions include 30 min at 37° C., 30 min at 20° C., and storage at 4° C.

4) Step 4 (rolling circle replication): In a 1.5 ml centrifuge tube, 100 ng of the gapped circular DNA sample produced in Step 3 was subjected to rolling circle replication by incubation at 30° C. for 4-8 hrs, and then inactivated at 80° C. for 20 min. The reaction system for rolling circle replication is (the final reaction system is 4 ml, with 1 ml/tube of reaction):

| Reagent | uL |
|---|---|
| USER treatment sample | 400 |
| 10*phi29 DNA polymerase buffer | 400 |
| dNTP(10 mM) | 200 |
| BSA(2 mg/mL) | 400 |
| phi29 DNA polymerase | 200 |
| ddH2O | 2400 |

5) Step 5 (annealing—auto-folding): The product after rolling circle replication was annealed by cooling to form a designed hairpin structure, where the annealing procedure was 5 min at 80° C., cooling to 65° C. at 0.1° C./s, 5 min at 65° C., cooling to 42° C. at 0.1° C./s, 5 min at 42° C., 5 min at 37° C., cooling to 4° C. at 0.1° C./s, and then stored at 4° C.

Figure 9:
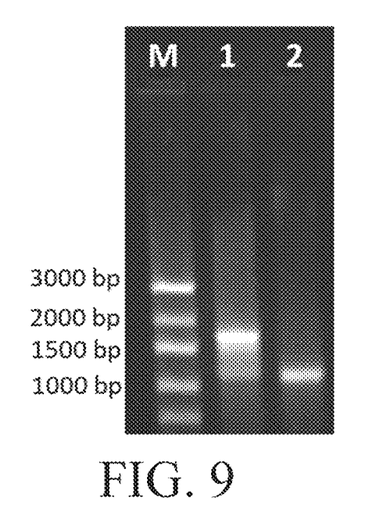
FIG. 9 shows the result of agarose gel electrophoresis after magnetic bead purification of the product obtained after the hairpin structure is cleaved by BspQI restriction endonuclease in Example 3.

6) Step 6 (restriction endonuclease cleavage-release of the target fragment, that is, the long single-stranded monomer): 150 ul of 10× restriction endonuclease buffer, and 20 ul of the selected type II restriction endonuclease were added to the above reaction product, and ddH$_2$O was added up to a volume of 1500 ul. The system was stood at an optimal reaction temperature for the restriction endonuclease for 60 min, and then thermally denatured and inactivated. The electropherogram of the crude reaction product is shown in FIG. 9.

7) Step 7 (purification and concentration): The cleavage product by restriction endonuclease contains the single-stranded DNA product of the target fragment and the hairpin structure. Since the length of the target sequence is >300 nt, agarose gel electrophoresis is used for extraction and purification. The electropherogram of the end product after purification is shown in FIG. 9, where Lane 1 is the crude product before purification, and Lane 2 is the purified product. The hairpin structure and the double-stranded DNA contaminant are effectively removed, the purity is 95%, and the sequence accuracy is 100%. Next generation sequencing (NGS) was used for sequence verification. The test result of the sequence is shown in FIG. 12, and is consistent with SEQ ID NO: 3.

As shown in the above three examples, the present method can be used to produce long single-stranded DNA with a length of 150-2500 nt. This method is applicable to sequences of various lengths, has low requirements on equipment and is easy to be scaled up for production. The purified long single-stranded DNA has a high purity and a sequence fidelity of 100%, thus being suitable for use as an efficient gene knock-in template for CRISPR gene editing.

What is claimed is:

1. A method for producing a target single-stranded DNA, comprising:
   (1) obtaining a template double-stranded DNA molecule consisting of a first strand and a reverse complementary second strand, wherein the sequence structure of the first strand is as shown in Formula (I):

5' left aptamer sequence-target single-stranded DNA sequence-right aptamer sequence 3'    (I)

wherein:
   the left aptamer sequence has a sequence structure of Formula: $X_nTX_qX_A$; and the right aptamer sequence has a sequence structure of Formula: $X_BX_q'X_{n-m}$,
   in which $X_n$ is a nucleotide sequence consisting of n nucleotides, where the 5'-terminal nucleotide is A and n is any integer of at least 4;
   $X_q$ is the sequence of a type II restriction endonuclease recognition site, and $X_q$ is not present in the target single-stranded DNA sequence; $X_q'$ is a reverse complementary sequence of $X_q$; $X_A$ and $X_B$ are 0 to several nucleotides, so that $X_qX_A$ and $X_BX_q'$ constitute the cleavage site of the type II restriction endonuclease respectively, to allow the type II restriction endonuclease to cleave at the 3' terminus of the $X_qX_A$ sequence and the 5' terminus of the $X_B X_q'$ sequence;
   $X_{n-m}$ is a sequence of n-m nucleotides from the 5' terminus of $X_n$, and m is an integer of 1-3; and
   A represents the adenine nucleotide; and T represents the thymine nucleotide;
   (2) with the template double-stranded DNA molecule as a template, performing PCR amplification using a forward primer and a reverse primer to obtain a product double-stranded DNA molecule comprising a first strand containing the target single-stranded DNA sequence and a reverse complementary second strand thereof;
   wherein the forward primer comprises a sequence of $X_nUX_qX_A$, and the reverse primer comprises a sequence of $X_{n-m}'X_q'X_B'$, in which $X_1$, $X_q$, $X_A$, and $X_B$ are the same as in (1); $X_{n-m}'$ is a reverse complementary sequence of $X_{n-m}$, with the T at the 3' terminus being replaced by U; $X_B'$ is a reverse complementary sequence of $X_B$; and U is the uracil nucleotide;
   (3) cleaving the product double-stranded DNA molecule at U contained in the two strands with a uracil-specific excision reagent to produce cohesive terminuses at the two ends of the product double-stranded DNA molecule;
   (4) ligating the two cohesive terminuses of the product double-stranded DNA molecule in the presence of a ligase, to form a circular double-stranded DNA having a gap in the first strand;
   (5) subjecting the gapped circular double-stranded DNA obtained in Step (4) to rolling circle replication, where the replication starts with the gap in the sense first strand of the product double-stranded DNA molecule and uses the second strand as the template, to obtain a replicon comprising multiple sequence structures as shown in the following formula (II) in tandem:

5'-$X_nTX_qX_A$-target single-stranded DNA sequence-$X_BX_q'$-3'    (II)

(6) annealing the replicon, so that a hairpin structure is formed between two adjacent target single-stranded DNA sequences in the replicon, wherein the hairpin structure consists of a sequence of $X_q'$ $X_nTX_q$;
   (7) treating the replicon with the type II restriction endonuclease, and cleaving at the 5' terminus and 3 terminus of the $X_BX_q'$ $X_nTX_qX_A$ sequence between adjacent target single-stranded DNA sequences to release multiple target single-stranded DNA sequences.

2. The method according to claim 1, wherein the type II restriction endonuclease is selected from AlwI, BbsI, BbvI, BceAI, BCIVI, BfuAI, BmrI, BpmI, BpuEI, BsaI, BseRI, BsgI, BsmAI, BsmBI, BsmFI, BspMI, BspQI, HphI, HpyAV, FokI, FauI, and HgaI.

3. The method according to claim 1, wherein the uracil-specific excision reagent is a uracil-specific excision enzyme.

4. The method according to claim 1, wherein the ligase is T4 DNA ligase.

5. The method according to claim 1, wherein steps (3) and (4) occur in the same reaction system in the presence of the uracil-specific excision reagent and the ligase.

6. The method according to claim 1, wherein the rolling circle replication is carried out using a DNA polymerase capable of continuous replication.

7. The method of claim 6, wherein the DNA polymerase is a phi29 DNA polymerase.

8. The method according to claim 1, wherein the type II restriction endonuclease is BspQI.

9. The method according to claim 8, wherein $X_qX_A$ has a sequence of GCTCTTCN, in which N is A, T, C or G; $X_BX_q'$ has a sequence of $N_1N_2N_3N_4$GAAGAGC, in which $N_1$, $N_2$, $N_3$, and $N_4$ are independently selected from A, T, C or G.

10. The method of claim 9, wherein $X_BX_q'$ has a sequence of CCTTGAAGAGC (SEQ ID NO:8).

11. The method according to claim 1, wherein n is 6-10.

12. The method according to claim 1, wherein n is 8.

13. The method according to claim 1, wherein m is 1.

14. The method according to claim 1, wherein $X_n$ has a sequence of AACTATAC, and $X_{n-m}$ has a sequence of AACTATA.

15. The method according to claim 1, where the target single-stranded DNA has a length of 150-2500 nt.

16. The method according to claim 1, comprising: performing sequence analysis of the target single-stranded DNA sequence before the template double-stranded DNA molecule is produced, and selecting a type II restriction endonuclease that has no cleavage site in the target single-stranded DNA sequence.

17. A kit for producing single-stranded DNA, comprising:
   a DNA polymerase suitable for polymerase chain reaction;
   a DNA ligase;
   a uracil specific excision reagent;
   a DNA polymerase suitable for rolling circle amplification;
   a type II restriction endonuclease,
   a left aptamer, having a sequence as shown in a formula of $X_nTX_qX_A$; and a right aptamer, having a sequence as shown in a formula of $X_BX_q'X_{n-m}$,
   wherein $X_n$ is a nucleotide sequence consisting of n nucleotides, where the 5'-terminal nucleotide is A and n is any integer of at least 4;
   $X_q$ is the sequence of a type II restriction endonuclease recognition site, and $X_q$ is not present in the target single-stranded DNA sequence; $X_q'$ is a reverse complementary sequence of $X_q$; $X_A$ and $X_B$ are 0 to several nucleotides, so that $X_qX_A$ and $X_BX_q'$ constitute a cleavage site of the type II restriction endonuclease respectively, to allow the type II restriction endonuclease to cleave at the 3' terminus of $X_A$ and the 5' terminus of the $X_B$;

$X_{n-m}$ is a sub-sequence of n-m nucleotides from the 5' terminus of $X_n$, and m is an integer of 1-3; and A represents the adenine nucleotide; and T represents the thymine nucleotide; and a forward primer having a sequence of $X_n U X_q X_A$, and a reverse primer having a sequence of $X_{n-m}' X_q' X_B'$, wherein $X_n$, $X_q$, $X_A$, and $X_B$ are the same as in the aptamer; and $X_{n-m}'$ is a reverse complementary sequence of $X_{n-m}$, with T at the 3' terminus being replaced by U; $X_B'$ is a reverse complementary sequence of $X_B$; and U is the uracil nucleotide; and wherein the forward primer and the reverse primer allow PCR amplification using the target DNA sequence as a template.

18. The kit according to 17, wherein the DNA ligase and the uracil-specific excision reagent are placed in the same container.

19. The kit of claim 17, wherein the DNA ligase is T4 DNA ligase, the uracil specific excision reagent is uracil specific excision enzyme, and the DNA polymerase is a phi29 DNA polymerase.

* * * * *

```
                              SEQUENCE LISTING

<160> NUMBER OF SEQ ID NOS: 8

<210> SEQ ID NO 1
<211> LENGTH: 253
<212> TYPE: DNA
<213> ORGANISM: Artificial Sequence
<220> FEATURE:
<223> OTHER INFORMATION: Synthetic Construct

<400> SEQUENCE: 1
tcaaacgcta ctactattag tagaattgat gccaccttt  cagctcgcgc cccaaatgaa     60
aatatagcta aacaggttat tgaccatttg cgaaatgtat ctaatggtca aactaaatct    120
actcgttcgc agaattggga atcaactgtt acatggaatg aaacttccag acaccgtact    180
ttagttgcat atttaaaaca tgttgagcta cagcaccaga ttcagcaatt aagctctaag    240
ccatccgcaa aaa                                                       253

<210> SEQ ID NO 2
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 2
tcaaacgcta ctactattag tagaattgat gccaccttt  cagctcgcgc cccaaatgaa     60
aatatagcta aacaggttat tgaccatttg cgaaatgtat ctaatggtca aactaaatct    120
actcgttcgc agaattggga atcaactgtt acatggaatg aaacttccag acaccgtact    180
ttagttgcat atttaaaaca tgttgagcta cagcaccaga ttcagcaatt aagctctaag    240
ccatccgcaa aaatgacctc ttatcaaaag gagcaattaa aggtactctc taatcctgac    300
ctgttggagt ttgcttccgg tctggttcgc tttgaagctc gaattaaaac gcgatatttg    360
aagtctttcg ggcttcctct taatcttttt gatgcaatcc gctttgcttc tgactataat    420
agtcagggta aagacctgat ttttgattta tggtcattct cgttttctga actgtttaaa    480
gcatttgagg gggattcaat gaatatttat gacgattccg cagtattgga cgctatccag    540
tctaaacatt ttactattac cccctctggc aaaacttctt ttgcaaaagc ctctcgctat    600
tttggttttt atcgtcgtct ggtaaacgag ggttatgata gtgttgctct tactatgcct    660
cgtaattcct tttggcgtta tgtatctgca ttagttgaat gtggtattcc taaatctcaa    720
ctgatgaatc tttctacctg taataatgtt gttccgttag ttcgttttat taacgtagat    780
ttttcttccc aacgtcctga ctggtataat gagccagttc ttaaaatcgc ataaggtaat    840
tcacaatgat taaagttgaa attaaaccat ctcaagccca atttactact cgttctggtg    900
tttctcgtca gggcaagcct tattcactga atgagcagct ttgttacgtt gatttgggta    960
atgaatatcc ggttcttgtc aagattactc ttgatgaagg tcagccagcc tatgcgcctg   1020
gtctgtacac cgttcatctg tcctctttca aagttggtca gttcggttcc cttatgattg   1080
accgtctgcg cctcgttccg gctaagtaac atggagcagg tcgcggattt cgacacaatt   1140
tatcaggcga tgatacaaat ctccgttgta ctttgtttcg cgcttggtat aatcgctggg   1200
ggtcaaagat gagtgtttta gtgtattctt tcgcctcttt cgttttaggt tggtgccttc   1260
```

-continued

```
gtagtggcat tacgtatttt acccgtttaa tggaaacttc ctcatgaaaa agtctttagt    1320
cctcaaagcc tctgtagccg ttgctaccct                                     1350

<210> SEQ ID NO 3
<211> LENGTH: 2350
<212> TYPE: DNA
<213> ORGANISM: Artificial Sequence
<220> FEATURE:
<223> OTHER INFORMATION: Synthetic Construct

<400> SEQUENCE: 3
tcaaacgcta ctactattag tagaattgat gccacctttt cagctcgcgc cccaaatgaa      60
aatatagcta aacaggttat tgaccatttg cgaaatgtat ctaatggtca aactaaatct     120
actcgttcgc agaattggga atcaactgtt acatggaatg aaacttccag acaccgtact     180
ttagttgcat atttaaaaca tgttgagcta cagcaccaga ttcagcaatt aagctctaag     240
ccatccgcaa aaatgacctc ttatcaaaag gagcaattaa aggtactctc taatcctgac     300
ctgttggagt ttgcttccgg tctggttcgc tttgaagctc gaattaaaac gcgatatttg     360
aagtctttcg ggcttcctct taatcttttt gatgcaatcc gctttgcttc tgactataat     420
agtcagggta aagacctgat ttttgattta tggtcattct cgttttctga actgtttaaa     480
gcatttgagg gggattcaat gaatatttat gacgattccg cagtattgga cgctatccag     540
tctaaacatt ttactattac cccctctggc aaaacttctt ttgcaaaagc ctctcgctat     600
tttggttttt atcgtcgtct ggtaaacgag ggttatgata tgttgctct tactatgcct     660 cgtaattcct tttggcgtta tgtatctgca ttagttgaat gtggtattcc taaatctcaa     720
ctgatgaatc tttctacctg taataatgtt gttccgttag ttcgttttat taacgtagat     780
ttttcttccc aacgtcctga ctggtataat gagccagttc ttaaaatcgc ataaggtaat     840
tcacaatgat taaagttgaa attaaaccat ctcaagccca atttactact cgttctggtg     900
tttctcgtca gggcaagcct tattcactga atgagcagct ttgttacgtt gatttgggta     960
atgaatatcc ggttcttgtc aagattactc ttgatgaagg tcagccagcc tatgcgcctg    1020
gtctgtacac cgttcatctg tcctctttca aagttggtca gttcggttcc cttatgattg    1080
accgtctgcg cctcgttccg gctaagtaac atggagcagg tcgcggattt cgacacaatt    1140
tatcaggcga tgatacaaat ctccgttgta ctttgtttcg cgcttggtat aatcgctggg    1200
ggtcaaagat gagtgtttta gtgtattctt tcgcctcttt cgttttaggt tggtgccttc    1260
gtagtggcat tacgtatttt acccgtttaa tggaaacttc ctcatgaaaa agtctttagt    1320
cctcaaagcc tctgtagccg ttgctaccct cgttccgatg ctgtctttcg ctgctgaggg    1380
tgacgatccc gcaaaagcgg cctttaactc cctgcaagcc tcagcgaccg aatatatcgg    1440
ttatgcgtgg gcgatggttg ttgtcattgt cggcgcaact atcggtatca agctgtttaa    1500
gaaattcacc tcgaaagcaa gctgataaac cgatacaatt aaaggctcct tttggagcct    1560
ttttttttgg agattttcaa cgtgaaaaaa ttattattcg caattccttt agttgttcct    1620
ttctattctc actccgctga aactgttgaa agttgtttag caaaccccca tacagaaaat    1680
tcatttacta acgtctggaa agacgacaaa actttagatc gttacgctaa ctatgagggt    1740
tgtctgtgga atgctacagg cgttgtagtt tgtactggtg acgaaactca gtgttacggt    1800
acatgggttc ctattgggct tgctatccct gaaaatgagg gtggtggctc tgagggtggc    1860
ggttctgagg gtggcggttc tgagggtggc ggtactaaac ctcctgagta cggtgataca    1920
cctattccgg gctatactta tcaaccctct cgacggca cttatccgcc tggtactgag    1980
```

```
caaaaccccg ctaatcctaa tccttctctt gaggagtctc agcctcttaa tactttcatg   2040
tttcagaata ataggttccg aaataggcag ggggcattaa ctgtttatac gggcactgtt   2100
actcaaggca ctgaccccgt taaaacttat taccagtaca ctcctgtatc atcaaaagcc   2160
atgtatgacg cttactggaa cggtaaattc agagactgcg ctttccattc tggctttaat   2220
gaggatccat tcgtttgtga atatcaaggc caatcgtctg acctgcctca acctcctgtc   2280
aatgctggcg gcggctctgg tggtggttct ggtggcggct ctgagggtgg tggctctgag   2340
ggtggcggtt                                                         2350

<210> SEQ ID NO 4
<211> LENGTH: 17
<212> TYPE: DNA
<213> ORGANISM: Artificial Sequence
<220> FEATURE:
<223> OTHER INFORMATION: Synthetic Construct

<400> SEQUENCE: 4
aactatactg ctcttca                                                 17

<210> SEQ ID NO 5
<211> LENGTH: 18
<212> TYPE: DNA
<213> ORGANISM: Artificial Sequence
<220> FEATURE:
<223> OTHER INFORMATION: Synthetic Construct

<400> SEQUENCE: 5
ccttgaagag caactata                                                18

<210> SEQ ID NO 6
<211> LENGTH: 17
<212> TYPE: DNA
<213> ORGANISM: Artificial Sequence
<220> FEATURE:
<223> OTHER INFORMATION: Forward primer with U modification

<400> SEQUENCE: 6
aactatacug ctcttca                                                 17

<210> SEQ ID NO 7
<211> LENGTH: 18
<212> TYPE: DNA
<213> ORGANISM: Artificial Sequence
<220> FEATURE:
<223> OTHER INFORMATION: Reverse primer with U modification

<400> SEQUENCE: 7
tatagtugct cttcaagg                                                18

<210> SEQ ID NO 8
<211> LENGTH: 11
<212> TYPE: DNA
<213> ORGANISM: Artificial Sequence
<220> FEATURE:
<223> OTHER INFORMATION: Synthetic Construct

<400> SEQUENCE: 8
ccttgaagag c                                                       11
```